United States Patent [19]

Hara

[11] Patent Number: 4,961,064
[45] Date of Patent: Oct. 2, 1990

[54] OIL LEAKAGE SENSOR

[76] Inventor: Sachio Hara, 8-2-813, Toyooka 1-Chome, Iruma-shi, Saitama, Japan

[21] Appl. No.: 435,643

[22] Filed: Nov. 13, 1989

[30] Foreign Application Priority Data

Dec. 8, 1988 [JP] Japan .................. 63-159010

[51] Int. Cl.$^5$ .......... H01C 1/02; H01C 7/00; H01C 8/00
[52] U.S. Cl. .................. 338/231; 338/34; 338/225
[58] Field of Search .............. 338/231, 223, 225, 54, 338/55, 34

[56] References Cited

U.S. PATENT DOCUMENTS 4,125,822 11/1978 Perren et al. .................. 338/223 X
4,862,066 8/1989 Sato et al. .................. 338/34 X

FOREIGN PATENT DOCUMENTS 0170468 2/1986 European Pat. Off. ............ 338/225

Primary Examiner—Bruce A. Reynolds
Assistant Examiner—Marvin M. Lateef

[57] ABSTRACT

An oil-leakage sensor formed from a porous water-repellent resin admixed with fine electrically conductive carbon particles coated with a water-repelling layer.

3 Claims, 1 Drawing Sheet

OIL LEAKAGE SENSOR

FIELD OF THE INVENTION

The invention relates to the field of oil leakage sensors wherein a resistor changes its resistance when a hydrocarbon or solvent material penetrates the water-repellent covering of the resistor.

BACKGROUND OF THE INVENTION

Conventional oil leakage sensors are equipped with a resistor which comprises a drawn porous polytetrafluoroethylene resin with admixed fine carbon particles, and a covering material comprising drawn polytetrafluoroethylene which covers the resistor.

In oil leakage sensors, when oil which has passed through the continuous pores of the covering material reaches and permeates the resistor, the jumping of electrons between the fine carbon particles of the resistor is hindered so that the resistance of the resistor increases. As a result, the leakage of oil is detected.

Oil leakage sensors of this type allow oil to invade the sensor. However, since the covering material is water-repellent, the sensors prevent invasion of the sensor by water.

When the above conventional oil leakage sensors described above used in a high-humidity environment, the resistance increases in the absence of oil permeation just as it does in the case of oil leakage, so that false detection occurs.

When a conventional oil leakage sensor is used over a long period of time, the surfaces of the fine carbon particles are oxidized by oxygen and ozone in the air so that oxygen-containing functional groups such as carboxyl groups, carbonyl groups, and hydroxyl groups are produced. As a result of this oxidation, the active hydrogen on the surfaces of the fine carbon particles increases.

Meanwhile, although the covering material is water-repellent, it cannot prevent invasion by water droplets which are smaller than the diameters of the fine pores in said material. Accordingly, when such a sensor is used in a high-humidity environment, fine droplets of water reach the interior portions of the resistor. Molecules of the water undergo a hydration reaction with the functional groups formed on the surfaces of the carbon particles or bond with the active hydrogen on the surfaces of the carbon particles so that the surface conditions of the fine carbon particles change and the strength of the electrostatic field increases. As a result, conductivity is lessened and the resistance of the resistor increases.

DESCRIPTION OF THE INVENTION

The present invention is an oil leakage sensor which is characterized by the fact that in an oil leakage sensor which is equipped with a resistor formed by mixing fine carbon particles with a water-repellent porous resin and a covering material which covers the resistor and which comprises a water-repellent porous resin, the surfaces of the fine carbon particles are covered with a water-repellent coating layer.

In the oil leakage sensor of the present invention, the surfaces of the carbon particles of the resistor are covered with a water-repellent coating layer. Even if fine droplets of water should pass through the pores of the covering material and permeate through the interiors of the fine pores of the resistor when the sensor is used in a high-humidity environment, the water-repellent coating agent will prevent or inhibit the bonding of the water with oxygen-containing functional groups and active hydrogen formed on the surfaces of the fine carbon particles. As a result, the strength of the electromagnetic field on the surfaces of the fine carbon particles is prevented from increasing, and the resistance of the resistor is therefore prevented from rising.

DESCRIPTION OF EMBODIMENTS OF THE INVENTION

Figure 1:
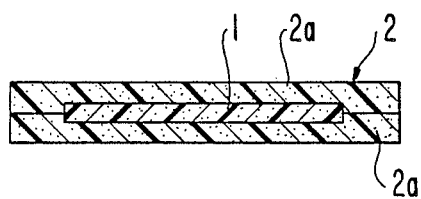
FIG. 1 describes a cross-section of the sensor.
Figure 2:
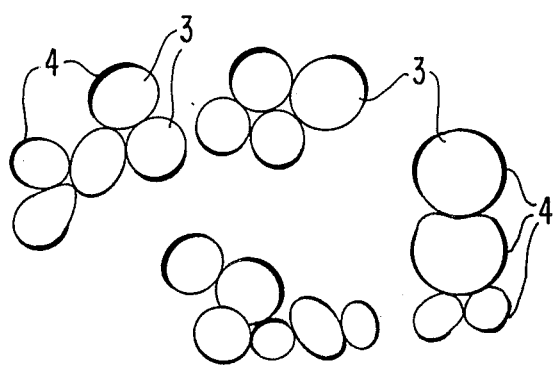
FIG. 2 shows the fine conductive carbon particles coated with a water-repelling material.

Referring now to the Figures to more carefully delineate the invention, FIG. 1 indicates a resistor comprising drawn porous polytetrafluoroethylene with admixed fine electrically conductive particles. All or part of this drawn porous polytetrafluoroethylene is fibrous in form and the spaces between the fibers form continuous fine pores. The carbon particles are supported by the fibers and are exposed inside the continuous fine pores. Resistor 1 is surrounded by a covering material 2 which comprises two strips of drawn porous polytetrafluoroethylene tape 2a that are joined together. The ends of respective lead wires (not shown in the figures) are attached to the ends of resistor 1. The opposite ends of the lead wires are led out to the exterior of covering material 2 and connected to a detector (not shown in the figures).

The oil leakage sensor is subjected to a hydrophobic treatment as follows. A liquid rubber type fluororesin coating agent (for example Eitoshiiru 1205, manufactured by Asahi Glass K. K.) is diluted with a solvent such as freon, and mixed with a setting agent to form a solution. This solution is then applied to the oil leakage sensor constructed as above. As a result, the solution penetrates through the continuous fine pores of covering material 2 and the fine pores of resistor 1. Afterward, the solution is dried and the solvent is removed. The sensor is then heated so that the coating agent is thermally set. As a result, a water-repellent coating layer 4 is formed on the surfaces of fine carbon particles 3 which face the interiors of the fine pores. This coating layer 4 occupies a portion of the surface of each carbon particle 3. Furthermore, this coating layer 4 is also formed on the interior surfaces of the fine pores of covering material 2 and resistor 1, i.e. on the surfaces of the fibers making up the parts.

A weak electric current is passed through resistor 1 of the oil leakage sensor and the resistance value of resistor 1 is detected by the detector. In the absence of any oil leakage, resistor 1 is conductive as a result of the flow or jumping of electrons between the particles 3, as a result, the resistance value of the resistor is low. Since coating layer 4 is formed only on the portions of the surfaces of carbon particles 3 that protrude into the interiors of the fine pores in the polytetrafluoroethylene resin (which constitutes the water-repellent supporting matrix), the coating layer 4 does not impede the conductivity.

When the oil leakage sensor is used in a high-humidity environment, fine droplets of water pass through the continuous fine pores of covering material 2 and penetrate into the continuous fine pores of resistor 1. However, since coating layer 4 is formed on the surfaces of carbon particles 3, the bonding of water molecules with oxygen-containing functional groups or active hydrogen present on the surfaces of carbon particles 3 will be prevented or inhibited. As a result, the resistance of the resistor 1 will not rise in the absence of oil leakage. Accordingly, false detection can be prevented.

In the case of oil leakage, the leaking oil will pass through the continuous fine pores of covering material 2 and penetrate into the continuous fine pores of resistor 1. This oil penetrates to the surfaces of fine conductive carbon particles 3 and fills the spaces between the particles 3. As a result, the resistance value of resistor 1 rises, which is detected by the detector, so that the oil leakage is detected. In this case, since coating layer will absorb and swell with oil, there is no hindrance of the oil leakage detection action.

The present invention is not limited to the practical example of application described above, various modifications are possible. For example, the oil leakage sensor could also be used to detect the leakage of organic solvents. In this specification, the term "oil" includes organic solvents. Furthermore, it would also be possible to form the coating layer over more or less the entire surface of each fine conductive carbon particle. In such a case, the conductivity of the resistor should not be adversely affected as long as the coating layer is extremely thin. A coating layer of silicone resin on the conductive carbon particles may be used instead of a fluorocarbon resin coating. As covering layer for the resistor portion of the detector may be used oil passable layers of porous silicone resin and porous polypropylene in addition to the preferred porous expanded polytetrafluoroethylene. Advantageously, in the present invention, a water-repellent coating layer is formed on the surfaces of the fine conductive carbon particles in an oil leakage detector. Accordingly, the bonding of water molecules to oxygen-containing functional groups or active hydrogen present on the surfaces of said fine carbon particles can be prevented or inhibited, and false detection can therefore be prevented.

I claim:
1. An oil-leakage sensor comprising:
   (a) a resistor formed of water-repellent porous resin having admixed fine electrically conductive carbon particles, said carbon particles being covered with an oil-penetrable water-repellent coating layer; and
   (b) a covering material surrounding said resistor which comprises a water-repellent porous resin.
2. A sensor of claim 1, wherein the water-repellent porous resin comprises porous expanded polytetrafluoroethylene.
3. A sensor of claim 2, wherein the water-repellent coating layer comprises a fluororesin.

* * * * *